US012004441B2

(12) United States Patent
Eda et al.

(10) Patent No.: US 12,004,441 B2
(45) Date of Patent: Jun. 11, 2024

(54) SOIL DENSITY PREDICTION FOR SUBSOIL CROPS

(71) Applicant: INTERNATIONAL BUSINESS MACHINES CORPORATION, Armonk, NY (US)

(72) Inventors: Sasikanth Eda, Vijayawada (IN); Sarbajit K. Rakshit, Kolkata (IN); Sachin Chandrakant Punadikar, Pune (IN); Sandeep Ramesh Patil, Pune (IN)

(73) Assignee: International Business Machines Corporation, Armonk, NY (US)

( * ) Notice: Subject to any disclaimer, the term of this patent is extended or adjusted under 35 U.S.C. 154(b) by 786 days.

(21) Appl. No.: 17/082,315

(22) Filed: Oct. 28, 2020

(65) Prior Publication Data

US 2022/0124961 A1   Apr. 28, 2022

(51) Int. Cl.
*A01B 79/00* (2006.01)
*A01G 7/00* (2006.01)
*G01N 9/26* (2006.01)
*G01N 33/24* (2006.01)
(Continued)

(52) U.S. Cl.
CPC .............. *A01B 79/005* (2013.01); *A01G 7/00* (2013.01); *G01N 9/26* (2013.01); *G01N 33/246* (2013.01); *G06F 16/2379* (2019.01); *G06N 20/00* (2019.01); *G01N 2033/245* (2013.01)

(58) Field of Classification Search
CPC ... A01B 79/005; A01B 79/00; G06F 16/2379; G06F 16/23; G06F 16/20; G06F 16/00; A01G 7/00; G01N 9/26; G01N 33/246; G01N 2033/245; G01N 9/20; G01N 9/00; G01N 33/24; G01N 33/00; G01N 20/00
See application file for complete search history.

(56) References Cited

U.S. PATENT DOCUMENTS

| 8,712,148 B2 * | 4/2014 | Paris ......................... G06T 7/00 345/589 |
| 2018/0108123 A1 * | 4/2018 | Baurer ..................... A01G 2/00 |
| 2019/0170718 A1 | 6/2019 | Miresmailli |

FOREIGN PATENT DOCUMENTS

| CN | 104236624 B | 9/2016 |
| CN | 110115129 A | 8/2019 |
| JP | 2018029517 A | 3/2018 |

OTHER PUBLICATIONS

"Unearthing Underground Crops Back to the Roots", Cropscience Bayer, Jan. 9, 2018; Retrieved from the Internet on Feb. 26, 2020, 2 pages, <URL: https://www.cropscience.bayer.co.za/en/News/Articles/Back-to-the-roots>.

(Continued)

*Primary Examiner* — Christopher J. Novosad
(74) *Attorney, Agent, or Firm* — Nicholas A. Welling (57) ABSTRACT

This is an approach to the prediction of soil density and subsoil crop growth. The approach may include subsoil sensor which can monitor changes in soil pressure and moisture conditions. The sensor data can be sent to a computer module which can process the data using a machine learning model predicting the soil density around a subsoil crop and the yield of the subsoil crop. A soil maintenance plan can be generated from the soil density prediction and/or the crop yield prediction. The soil maintenance plan can be sent to soil management robots, which can execute the soil maintenance plan.

20 Claims, 6 Drawing Sheets

(51) Int. Cl.
*G06F 16/23* (2019.01)
*G06N 20/00* (2019.01)

(56) References Cited

OTHER PUBLICATIONS

Mell, et al., "The NIST Definition of Cloud Computing", National Institute of Standards and Technology, Special Publication 800-145, Sep. 2011, 7 pages.

* cited by examiner

SOIL DENSITY PREDICTION FOR SUBSOIL CROPS

BACKGROUND OF THE INVENTION

The present invention relates generally to soil density prediction, and more specifically, to soil density prediction and soil management for subsoil crops.

Subsoil crops require loose nutrient dense soil to flourish and produce high yields. Many subsoil crops are staple foods in many countries around the world. With the increase in population, consistent yields of calorically dense foods are imperative to ensure sufficient food supplies. Current methods of monitoring the health of subsoil crops include soil sampling and monitoring the above-ground anatomy of crops for incremental changes.

SUMMARY

Embodiments of the present disclosure include a method, computer program, and system for soil density prediction for subsoil crops. A processor can retrieve an input from at least one subsoil sensor. The processor can analyze the input retrieved from the subsoil sensor. The processor can generate a soil maintenance plan for a subsoil crop based on the analyzing. The processor can execute the soil maintenance plan by a soil maintenance robot.

The above summary is not intended to describe each illustration or every implementation of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

The embodiments depicted and described herein recognize the need to ensure loose and loamy nutrient rich soil surrounding subsoil crops. Further, ensuring loose soil and managing moisture, pest infestation, and nutrient content can ensure higher yields of subsoil crops for users of embodiments of the invention.

In one embodiment of the invention, one or more subsoil sensors can monitor data such as, but not limited to, pressure and moisture changes of the soil surrounding a planter hill. A planter hill is a mound of dirt created around the base of a subsoil crop. One reason for forming a planter hill is to prevent shallow subsoil crop organs from inadvertently being exposed to the surface. The data from the subsoil sensors can be sent to a server for analysis and archiving. The server can have a module with machine learning capabilities for predicting soil congestion conditions wherein an associated model is trained with historical data such as, but not limited to, pressure sensor readings, moisture sensor readings and weather data. The machine learning functionality can predict the level of soil congestion based on the machine learning model. The predicted soil congestion level can then be transferred to the soil maintenance module where the soil maintenance module can generate a soil maintenance plan for operations such as, but not limited to, loosening the soil, adding additional nutrients to the soil, eradicating pests, and/or spreading out the organs of the subsoil crop. The soil maintenance plan can be transferred to a soil management robot having appendages suitable for at least aerating the soil in a sufficiently gentle manner to loosen the soil and/or adding nutrients in soil maintenance plan predicted areas.

In another embodiment, the server can have a module capable of predicting the yield of the subsoil crop, including the growth pattern and size of the subsoil crop organs. The soil maintenance module can account for the growth pattern and size of the subsoil crop organs and can generate a soil maintenance plan that can be sent to the soil management robot. The soil management robot can adjust the soil around the planter hill to ensure there is sufficient room for the subsoil crop organ to grow to optimize crop yield.

In another embodiment, a plurality of sensors can be dispersed throughout a planter hill of a specific subsoil crop. The sensors can measure parameters such as, but not limited to, pressure changes, temperature fluctuations, moisture, sensor depth, and vibrations. The measurements can be sent to a server with a soil density module and a yield prediction module.

In describing embodiments in detail with reference to the figures, it should be noted that references in the specification to "an embodiment," "other embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, describing a particular feature, structure or characteristic in connection with an embodiment, one skilled in the art has the knowledge to affect such feature, structure or characteristic in connection with other embodiments whether or not explicitly described.

Figure 1:
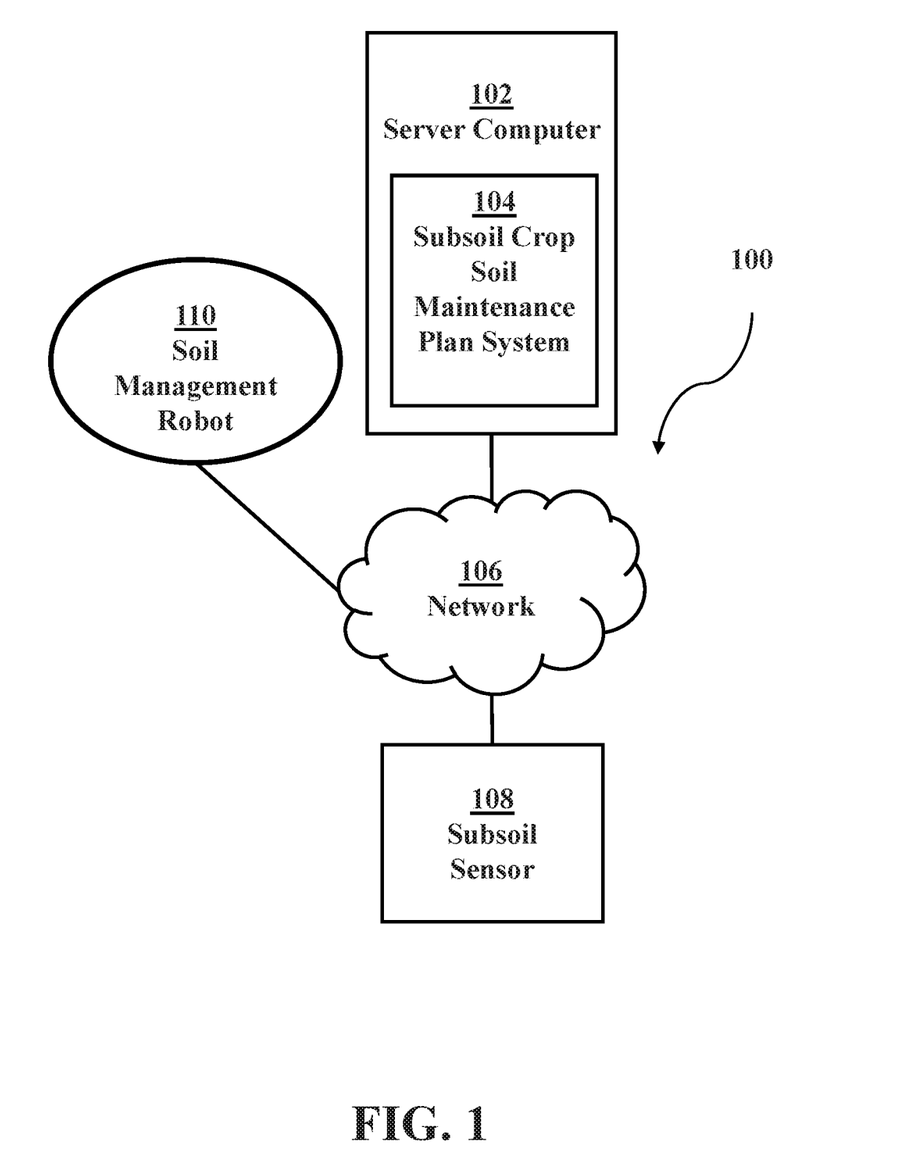
FIG. 1 is a functional block diagram generally depicting a subsoil crop soil density prediction environment, in accordance with an embodiment of the present invention.

FIG. 1 is a functional block diagram illustrating, generally, a subsoil crop soil density prediction environment 100. The subsoil crop soil density prediction environment 100 comprises subsoil crop soil maintenance plan system 104 operational on server computer 102, network 106, subsoil sensor 108, and soil management robot 110.

Server computer 102 can be a standalone computing device, management server, a web server, a mobile computing device, or any other electronic device or computing system capable of receiving, sending, and processing data.

In other embodiments, server computer 102 can represent a server computing system utilizing multiple computers as a server system. In another embodiment, server computer 102 can be a laptop computer, a tablet computer, a netbook computer, a personal computer, a desktop computer, or any programmable electronic device capable of communicating with other computing devices (not shown) within the subsoil crop soil density prediction and soil management environment 100 via network 106. It should be noted, while one server computer is shown in FIG. 1, there can be any number of server computers within subsoil crop soil density prediction and soil management environment 100.

In another embodiment, server computer 102 represents a computing system utilizing clustered computers and components (e.g., database server computers, application server computers, etc.) that act as a single pool of seamless resources when accessed within the subsoil crop soil density prediction and soil management environment 100. Server computer 102 can include internal and external hardware components, as depicted and described in further detail with respect to FIG. 4.

Network 106 can be, for example, a local area network (LAN), a wide area network (WAN) such as the Internet, or a combination of the two, and can include wired, wireless, or fiber optic connections. In general, network 106 can be any combination of connections and protocols that will support communications between server computer 104, subsoil sensor 108 and soil management robot 110.

Figure 4:
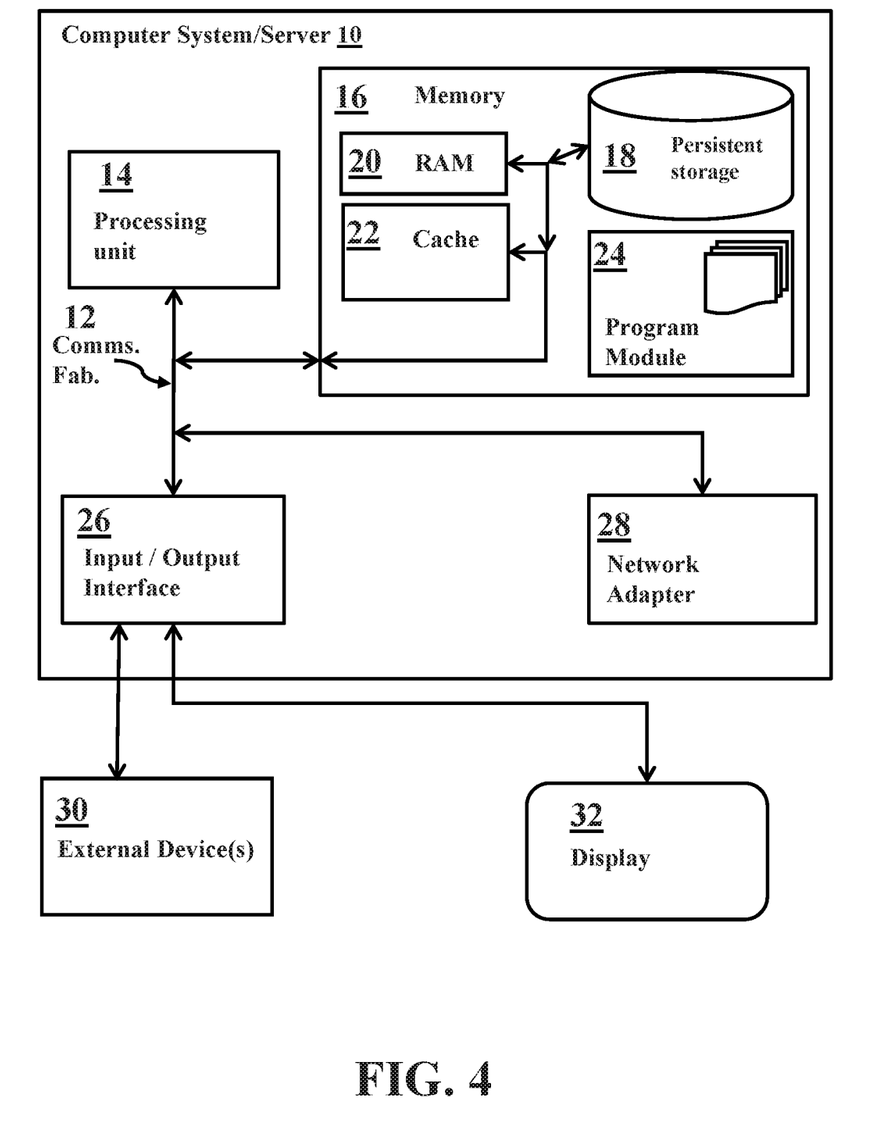
FIG. 4 is a functional block diagram of components of an exemplary computer within a subsoil crop soil density prediction environment, in accordance with an embodiment of the present invention.

Subsoil sensor 108 can be a sensor which is placed into the soil surrounding a subsoil crop and can monitor conditions of the soil around a subsoil crop (see FIG. 4). Subsoil sensor 108 can have the capability to measure soil pressure, for example, amount of static soil pressure, direction of soil pressure change, and rates of soil pressure change. Additionally, subsoil sensor 108 can have the capability to sense vibrations within the surrounding environment.

In some embodiments of the invention, subsoil sensor 108 can have capabilities to monitor soil moisture content, soil temperature, location (via Global Positioning Satellite (GPS) systems, radio frequency identification, WiFi beacon tracking) and soil nutrition content. Subsoil sensor 108 can receive the measurements in a variety of ways, including mechanical, optical, or measuring the movements of the sensors via GPS or other positioning mechanisms.

Additionally, in some embodiments of the invention a subsoil sensor 108 may communicate with other subsoil sensors or above ground sensors (not shown) to determine the depth at which the sensor is placed underground. Soil depth may also be determined by acoustic determination or optical sensing. Further, Subsoil sensor 108 can have the capability to connect to network 106 either through a wireless connection or a wired connection. For example, subsoil sensor may be wirelessly connected to a principal sensor in a field and the principal sensor relays the data to a server. A principal sensor may be a subsoil sensor or an above ground sensor with a continuous power supply (e.g. wired to an electrical grid) to prevent excess drain of the batteries of non-wired sensors. In some embodiments, the subsoil sensor 108 may be activated when a soil management robot 110 passes by on a maintenance operation and communicate with subsoil management robot 110. The subsoil sensor 108 sends its data to the soil management robot 110 and the soil management robot 110 relays the data to a server. It should be noted that while only one subsoil sensor is shown in FIG. 1, this is for simplicity, as multiple subsoil sensors may be incorporated in the soil surrounding a subsoil crop.

Soil management robot 110 can be a robot capable of manipulating the soil surrounding a subsoil crop and/or administering nutrition to the subsoil crop. Soil management robot 110, may have one or more methods of locomotion to reach the target subsoil crop (e.g. wheels, legs, propellers, tank treads, etc.) Further, soil management robot 110 may be automated or may be user operated. Additionally, soil management robot 110 may have a basic computing element as described in FIG. 4 for processing a soil maintenance plan. Soil management robot 110 may have appendages for manipulating the soil surrounding a subsoil crop. The appendages may include spear-like appendages or hollow cylinders capable of aerating soil by removing soil or inserting pressurized air at appropriate pressures without damaging the subsoil crop. Soil management robot 110 may have capabilities to image the roots and organs of a subsoil crop based on acoustic measurements of the surrounding ground to ensure the subsoil crop is not damaged during the soil manipulation process. Further, soil management robot 110 can manage the above soil portions of the subsoil crop, including but not limited to pruning, spraying substances (herbicides, insecticides, fertilizers), removing insects and other pests, and, taking measurements of the above ground portion of the subsoil crops.

Subsoil crop soil maintenance plan system (SCSMPS) 104 can be a computer module that can receive data collected by subsoil sensor 108 and can predict the soil density surrounding a specific crop. Further, SCSMPS 104 can have the capability to generate a subsoil crop yield prediction based on data gathered from subsoil sensor 108 and machine learning capabilities can be operational on SCSMPS 104. SCSMPS 104 can also have the capability to produce a soil nutrition plan based on the soil density prediction and/or the subsoil crop yield prediction. The soil nutrition plan can involve physical manipulation of soil, insect/pest removal, removing dead subsoil organs, clearing non-organic debris from subsoil crop organ growth path, or administering nutrients to the soil and/or subsoil crop.

Figure 2:
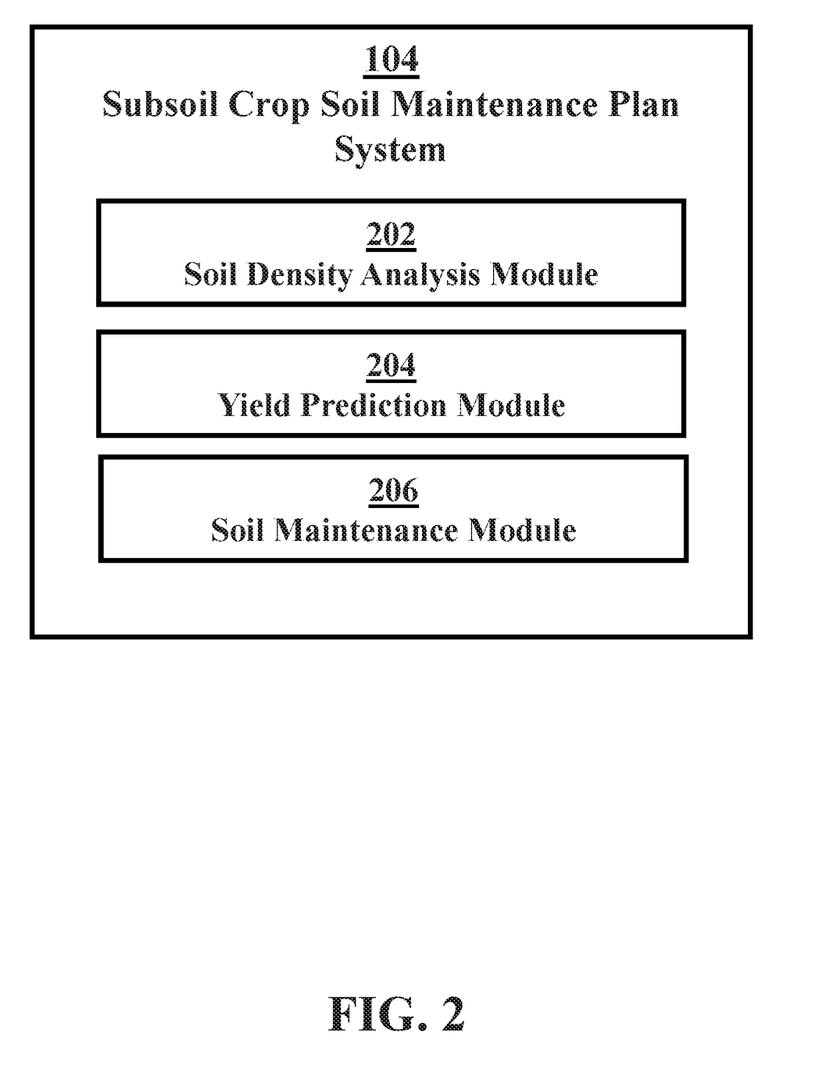
FIG. 2 is a functional block diagram depicting a subsoil crop soil maintenance plan system, in accordance with an embodiment of the present invention.

Now with reference to FIG. 2, a detailed block diagram of SCSMPS 104 is depicted, further comprising a soil density analysis module 202, a yield prediction module 204, and a soil maintenance module 206.

Soil density analysis module 202 can generate a soil density prediction based on data received from subsoil sensor 108. Soil density analysis module 202 can have an operational soil density prediction model. The soil density prediction model can have a knowledge corpus that includes historical data. Historical data within the knowledge corpus can include previous density readings, past weather (e.g. temperature, rainfall, prevailing winds, humidity, cloud coverage, etc.), pest conditions, weed conditions, video feed data, soil moisture levels, and soil nutrient levels. The soil density prediction model can predict the soil density and the root configuration of a specific crop (e.g. if the root system of the crop is too congested and thus would cause a poor yield.) Further, soil density analysis module can have the capability to determine looseness factor of the soil surrounding the subsoil crops. Looseness factor can be based multiple features, including, but not limited to temperature, latitude, longitude, precipitation, soil composition, subsoil crop growth rate, and fertilization timing. The soil density prediction model can predict the root configuration and location of dense soil based on the direction of real-time pressure reading from subsoil sensor 108. Additionally, in some embodiments, the soil density prediction model can be a reinforcement learning machine learning model (e.g.

Markov decision process, etc.) or a supervised learning model (e.g. linear regression, decision tree, random forest, etc.).

Further, in some embodiments, when multiple subsoil sensors 108 are placed within a planter hill associated with a subsoil crop the multiple readings can correlate to the location of the dense soil or congestion caused by subsoil crop roots or subsoil crop organs. Pressure and moisture readings form subsoil sensor 108 can be analyzed within the density prediction model to determine the density of the soil within of a planter hill associated with the subsoil sensor 108. It should be noted, the sensor data and real time weather data can be used to continuously update the soil density prediction model. Additionally, soil density prediction module 202 can analyze vibrations measured by subsoil sensor 108 to identify the movement of insects.

Yield prediction module 204 can provide the capability to predict the subsoil crop yield based on the soil density prediction received from soil density analysis module 202. Yield prediction module 204 can have an operational yield prediction model. The operational yield prediction model can be a machine learning model trained with historical data. The historical data can include previous soil density and crop organ congestion readings, as well as weather data, pest data, soil moisture data, and soil nutrition data. The machine learning model can be a supervised learning model (e.g. linear regression, decision tree, random forest, etc.) or a reinforcement model. The yield prediction model can have the capability to predict the soil density in the absence of a soil density analysis module, using the machine learning model. It should be noted that the yield prediction model can be dynamically updated using subsoil sensor 108 data, weather data, soil cultivation robot data, and actual subsoil crop yield data.

Soil maintenance module 206 can provide the capability to generate a soil maintenance plan based on the soil density prediction and/or the yield prediction and send the generated soil maintenance plan to soil management robot 110. Using a soil density prediction, soil maintenance module 206 can determine the location where the soil is compacted and send instructions to the soil management robot 110 to aerate the soil. These instructions can include the location of the planter hill associated with a sensor and the location of a dense area of soil or an area of subsoil crop organ congestion. Soil management robot 110 can also receive instructions regarding how to aerate the soil to prevent damage to the subsoil crop organs and can manipulate the soil to alleviate any congestion of the roots and subsoil crop organs. In some embodiments soil maintenance module 206 can use the yield prediction in conjunction with the subsoil density prediction to send instructions to soil maintenance management 110 to aerate the soil associated with a planter hill and administer nutrition to the planter hill. Nutrition can include, additional nutrients, pesticides, and herbicide. Further, the soil management robot 110 can remove weeds surrounding the planter hill based on the generated soil maintenance plan.

Figure 3:
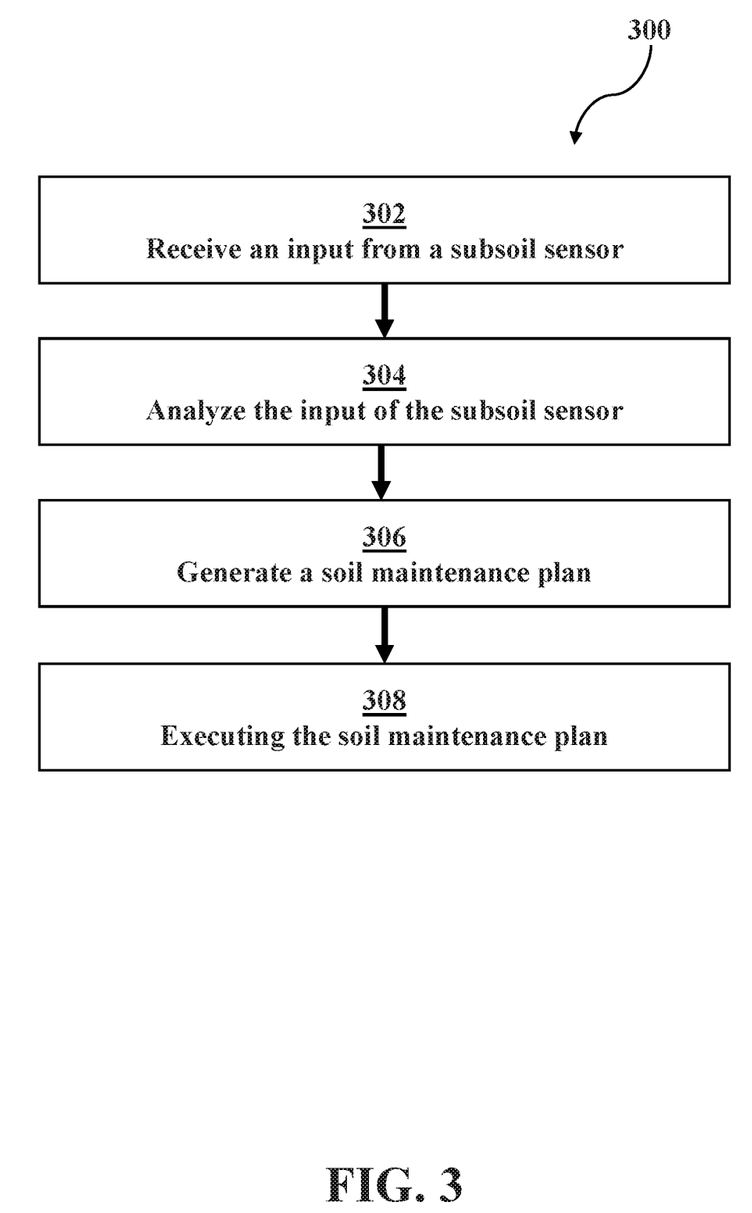
FIG. 3 is a flowchart depicting operational steps of a method for generating a subsoil crop soil density maintenance plan, in accordance with an embodiment of the present invention.

FIG. 3 depicts a flowchart showing operational steps of a method for generating a subsoil crop soil density maintenance plan, for an embodiment of the invention. At step 302, an input is received by SCSMPS 104 from subsoil sensor 108. At step 304, soil density analysis module 202 analyzes the input received from subsoil sensor 108. At step 306, soil maintenance module 206 generates a soil maintenance plan based on the analysis performed by soil density analysis module 202. At step 308, soil management robot 110 executes the soil maintenance plan generated by soil maintenance module 206.

FIG. 4 depicts computer system 10, an example computer system representative of a dynamically switching user interface computer 10. Computer system 10 includes communications fabric 12, which provides communications between computer processor(s) 14, memory 16, persistent storage 18, network adaptor 28, and input/output (I/O) interface(s) 26. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Computer system 10 includes processors 14, cache 22, memory 16, persistent storage 18, network adaptor 28, input/output (I/O) interface(s) 26 and communications fabric 12. Communications fabric 12 provides communications between cache 22, memory 16, persistent storage 18, network adaptor 28, and input/output (I/O) interface(s) 26. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses or a crossbar switch.

Memory 16 and persistent storage 18 are computer readable storage media. In this embodiment, memory 16 includes random access memory (RAM). In general, memory 16 can include any suitable volatile or non-volatile computer readable storage media. Cache 22 is a fast memory that enhances the performance of processors 14 by holding recently accessed data, and data near recently accessed data, from memory 16.

Program instructions and data used to practice embodiments of the present invention may be stored in persistent storage 18 and in memory 16 for execution by one or more of the respective processors 14 via cache 22. In an embodiment, persistent storage 18 includes a magnetic hard disk drive. Alternatively, or in addition to a magnetic hard disk drive, persistent storage 18 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Network adaptor 28, in these examples, provides for communications with other data processing systems or devices. In these examples, network adaptor 28 includes one or more network interface cards. Network adaptor 28 may provide communications through the use of either or both physical and wireless communications links. Program instructions and data used to practice embodiments of the present invention may be downloaded to persistent storage 18 through network adaptor 28.

I/O interface(s) 26 allows for input and output of data with other devices that may be connected to each computer system. For example, I/O interface 26 may provide a connection to external devices 30 such as a keyboard, keypad, a touch screen, and/or some other suitable input device.

External devices 30 can also include portable computer readable storage media such as, for example, thumb drives, portable optical or magnetic disks, and memory cards. Software and data used to practice embodiments of the present invention can be stored on such portable computer readable storage media and can be loaded onto persistent storage 18 via I/O interface(s) 26. I/O interface(s) 26 also connect to display 32.

Display 32 provides a mechanism to display data to a user and may be, for example, a computer monitor or virtual graphical user interface.

The components described herein are identified based upon the application for which they are implemented in a specific embodiment of the invention. However, it should be appreciated that any particular component nomenclature herein is used merely for convenience, and thus the invention should not be limited to use solely in any specific application identified and/or implied by such nomenclature.

The present invention may be a system, a method and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems) and computer program products according to embodiments of the invention. It is understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality and operation of possible implementations of systems, methods, and computer program products according to various embodiments of the present invention. In this regard, each block in the flowchart or block diagrams may represent a module, segment or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
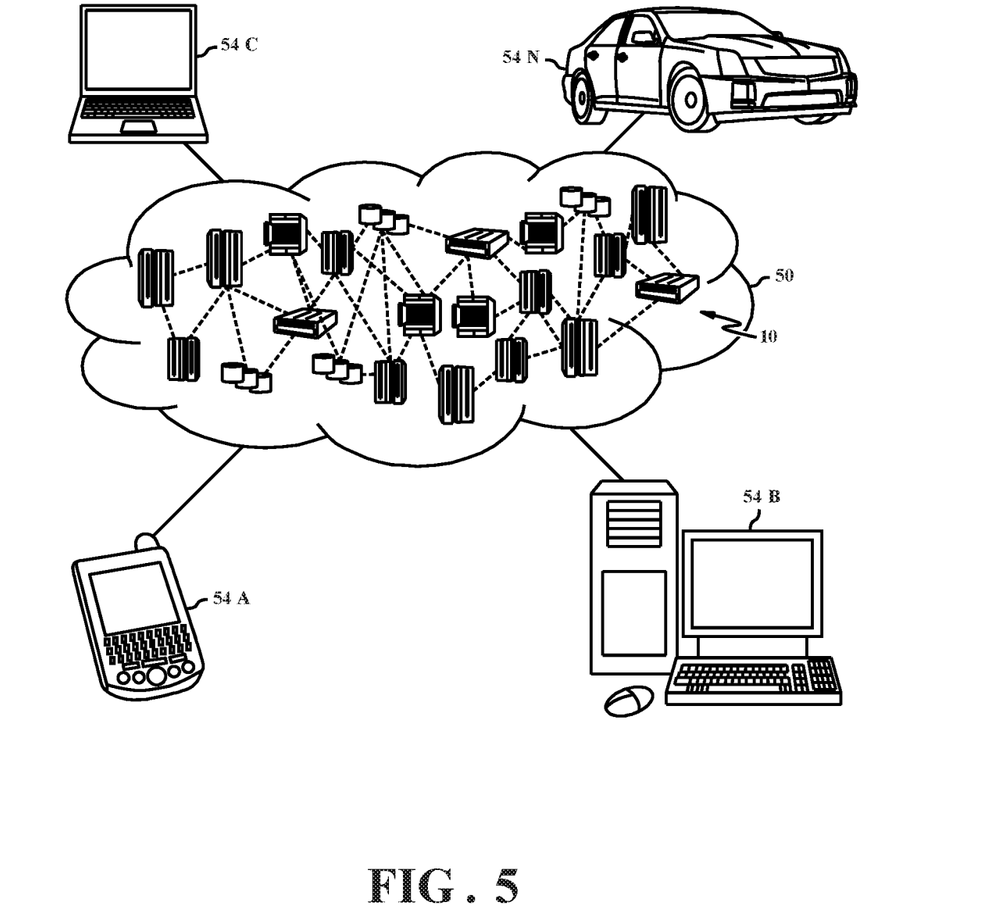
FIG. 5 is a diagram depicting a cloud computing environment, in accordance with an embodiment of the present invention.

FIG. 5 is a block diagram depicting a cloud computing environment 50 in accordance with at least one embodiment of the present invention. Cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 6:
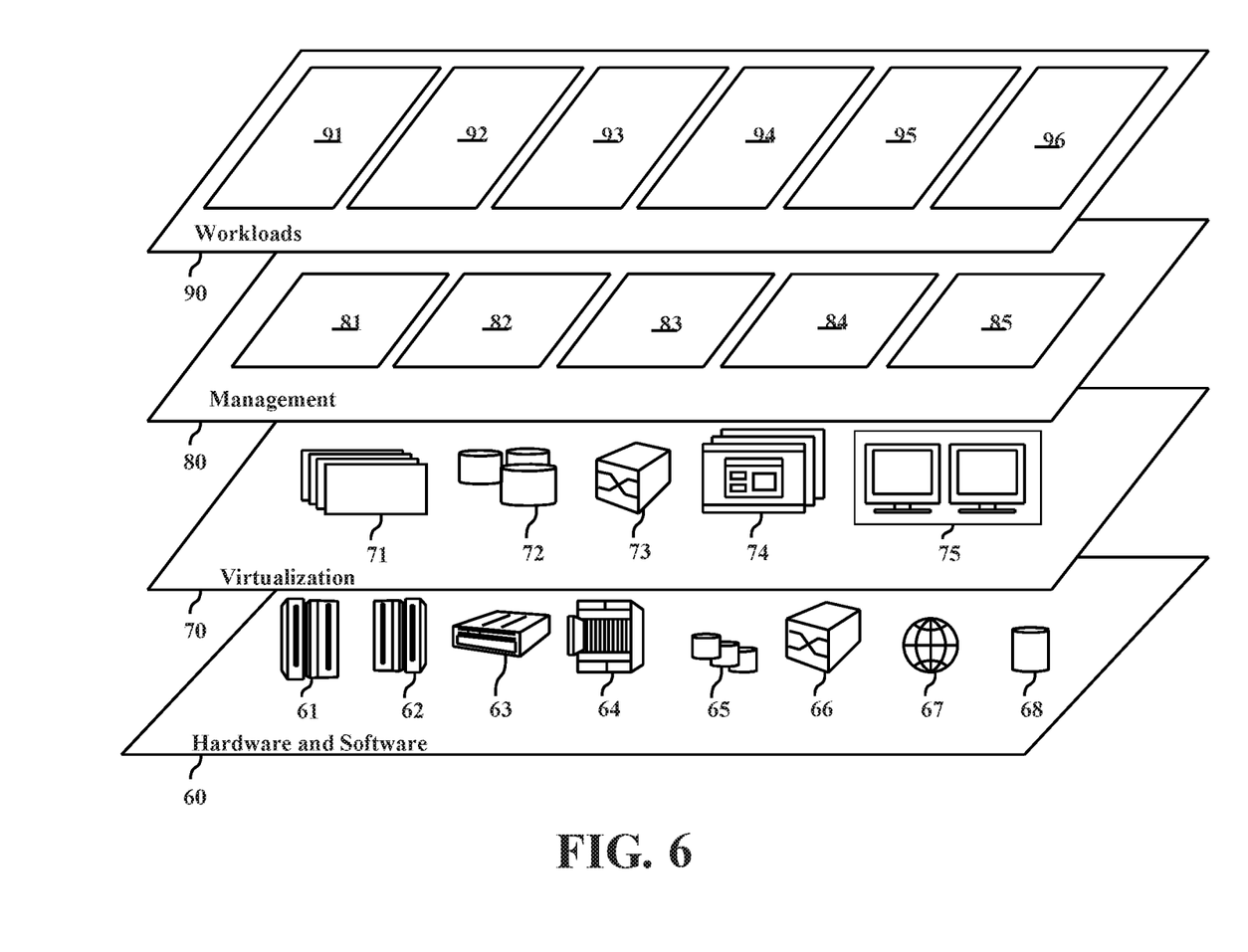
FIG. 6 is a functional block diagram depicting abstraction model layers, in accordance with an embodiment of the present invention.

FIG. 6 is a block diagram depicting a set of functional abstraction model layers provided by cloud computing environment 50 depicted in FIG. 5 in accordance with at least one embodiment of the present invention. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and subsoil crop soil density prediction application 96.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method for predicting soil density associated with a subsoil crop, the computer-implemented method comprising:
    retrieving, by one or more processors, an input from at least one subsoil sensor;
    analyzing, by the one or more processors, the input;
    generating, by the one or more processors, a soil maintenance plan for a subsoil crop based on the analyzing; and
    executing, by the one or more processors, the soil maintenance plan by a soil management robot.

2. The computer-implemented method of claim 1, wherein the input comprises:
    real-time soil data from the least one subsoil sensor associated with a crop.

3. The computer-implemented method of claim 2, wherein the real-time soil data is comprised of pressure variations from the in-ground sensors and moisture content of the soil.

4. The computer-implemented method of claim 3, wherein the analyzing further comprises:
    identifying, by the one or more processors, the pressure patterns created by the crop; and
    determining, by the one or more processors, subsoil crop root distribution, subsoil crop organ distribution, soil nutrition distribution, soil moisture content, and soil density based on the identifying.

5. The computer-implemented method of claim 1, wherein the input comprises historical data from a database.

6. The computer-implemented method of claim 5, further comprising:
    updating, by the one or more processors, the historical database with the real-time soil data and the soil maintenance plan.

7. The computer-implemented method of claim 1, further comprising:
    generating, by the one or more processors, a yield prediction for the subsoil crop based on the analyzing.

8. A computer system for predicting soil density associated with a subsoil crop, the system comprising:
    one or more computer processors;
    one or more computer readable storage media;
    computer program instructions;
    the computer program instructions being stored on the one or more computer readable storage media for execution by the one or more computer processors; and the computer program instructions including instructions to:
    retrieve an input from at least one subsoil sensor;
    analyze the input;
    generate a soil maintenance plan for a subsoil crop based on the analyzing; and
    execute the soil maintenance plan by a soil management robot.

9. The computer system of claim 8, wherein the input comprises:
    real-time soil data from the least one subsoil sensor associated with a crop.

10. The computer system of claim 9, wherein the real-time soil data is comprised of pressure variations from the in-ground sensors and moisture content of the soil.

11. The computer system of claim 8, wherein the input comprises historical data from a database.

12. The computer system of claim 11, further comprising:
    update the historical database with the real-time soil data and the soil maintenance plan.

13. The computer system of claim 8, further comprising:
generate a yield prediction for the subsoil crop based on the analyzing.

14. The computer system of claim 8, wherein the analyzing further comprises:
identifying, by the one or more processors, the pressure patterns created by the crop; and
determining, by the one or more processors, subsoil crop root distribution, subsoil crop organ distribution, soil nutrition distribution, soil moisture content, and soil density based on the identifying.

15. A computer program product for predicting soil density associated with a subsoil crop, the program instructions including instructions to:
retrieve an input from at least one subsoil sensor;
analyze the input;
generate a soil maintenance plan for a subsoil crop based on the analyzing; and
execute the soil maintenance plan by a soil management robot.

16. The computer program product of claim 15, wherein the input comprises:
real-time soil data from the least one subsoil sensor associated with a crop.

17. The computer program product of claim 16, wherein:
the real-time soil data is comprised of pressure variations from the in-ground sensors and moisture content of the soil.

18. The computer program product of claim 15, wherein the input comprises historical data from a database.

19. The computer program product of claim 18, the program instructions further comprising instructions to:
update the historical database with the real-time soil data and the soil maintenance plan.

20. The computer program product of claim 15, the program instructions further comprising instructions to:
generate a yield prediction for the subsoil crop based on the analyzing.

* * * * *